United States Patent [19]

Servas

[11] 4,096,070

[45] Jun. 20, 1978

[54] BLOOD FILTER

[75] Inventor: Francis Martin Servas, Belle Mead, N.J.

[73] Assignee: Johnson & Johnson, New Brunswick, N.J.

[21] Appl. No.: 756,220

[22] Filed: Jan. 3, 1977

[51] Int. Cl.² .............................................. B01D 29/06
[52] U.S. Cl. ................................ 210/448; 128/214 C; 210/DIG. 23
[58] Field of Search .............. 23/259, 292; 128/214 C, 128/214.2; 210/94, 446, 482, DIG. 23, 448; 222/80, 81; 285/8, 328

[56] References Cited

U.S. PATENT DOCUMENTS

| 2,874,981 | 2/1959 | Brady | 285/328 X |
| 3,224,799 | 12/1965 | Blose et al. | 285/328 X |
| 3,428,339 | 2/1969 | Haulik et al. | 285/328 X |
| 3,593,854 | 7/1971 | Swank | 210/446 X |
| 3,954,623 | 5/1976 | Hammer et al. | 128/214 C X |

Primary Examiner—Charles N. Hart
Assistant Examiner—Robert H. Spitzer

[57] ABSTRACT

In a blood filter of the type having a blood inlet spike which is to be inserted in a blood bag the improvement comprising the outer surface of the blood inlet spike having a roughness of from about 50 to 200 microinches.

2 Claims, 1 Drawing Figure

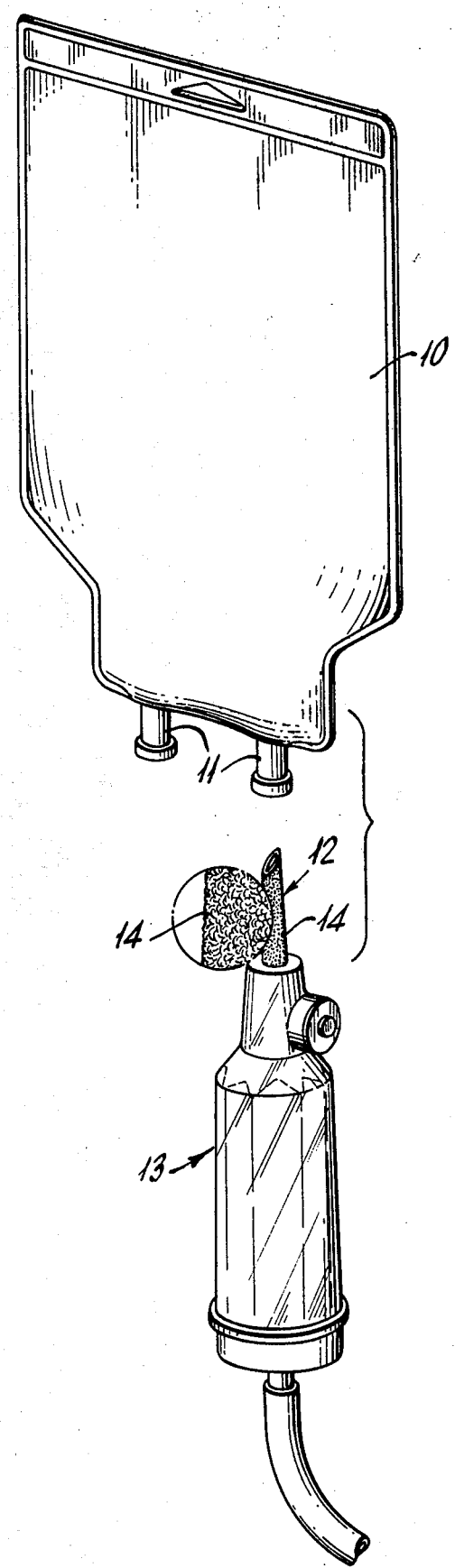

BLOOD FILTER

The present invention relates to blood filters especially blood filters of the type which are to used with blood bags in blood transfusions.

In transfusing blood it is a common practice to filter the blood as it is being administered to a patient. In recent years filters have been developed which have a blood inlet which is in the shape or configuration of a spike. The spiked blood inlet is inserted into a weakened portion of the blood bag so that it perforates and penetrates the bag and the inlet accepts the blood from the bag and presents it to the filter.

In such an operation there are a number of factors which must be taken into account. The bag, of course, must be constructed of a material that will withstand refrigeration and handling and will protect the blood. The bag must also have a suitable area that can be readily perforated or penetrated by the spike of the filter when it is desired to transfuse the blood. To accomplish this objective the filter itself must have a relatively strong rigid spike to which force can be applied to penetrate the blood bag. The spike must readily penetrate the bag and, of course, must be held by the penetrated portion during the transfusion of the blood and must eliminate the possibility of the filter falling out of the perforated opening of the bag.

One manner of accomplishing this desired result is to lubricate the spike of the filter with a petroleum jelly or the like. If just the right amount of such lubricant is used, the spike may be readily inserted in the bag and will be held by the bag during use. However, it is very difficult to be certain that exactly the correct amount of lubricant is placed on each spike during the manufacture of the filter. What I have discovered is a new blood spike which eliminates the necessity for lubricating the spike. Furthermore, my new blood filter spike is more economical to produce and can be produced with excellent reproducibility. My improved blood filter having my improved spike can be readily inserted into a blood bag and will be held by that blood bag with positive force.

In accordance with the present invention I have discovered an improved blood filter wherein the blood inlet spike has a roughened outer surface of from about 50 to 200 microinches. Preferably in my new and improved blood filter, the outside surface of the inlet spike has a surface roughness of from 90 to 130 microinches.

The invention will be more fully described in conjunction with the accompanying FIGURE which shows the blood bag 10 and the perforated opening 11 therein in perspective along with the improved blood spike 12 of the filter 13 of the present invention.

Blood bags are generally made from plastic materials such as polyvinyl chloride, polyethylene, polypropylene and the like. These are materials which are inert in contact with blood, may be sterilized and are suitable for storing blood. The bags themselves are generally rectangular in shape and are in a pouch or sack-type configuration. Along one edge of the bag is a sealed outlet which is to be punctured by some suitable means when the blood is to be transfused. This outlet is generally cylindrical in shape and of a diameter such as to accept inlet spikes from the filter or from an administration set. The outlet has a thin membrane closing the outlet which may be readily punctured.

Referring to the FIGURE, there is shown such a blood bag 10 having a pair of outlets 11 at its lower end. Each outlet has a thin membrane closing the outlet. Either outlet may be used when administering blood. The membrane is punctured by a suitable inlet spike 12 of a filter 13. The inlet spike of the filter has an outside diameter substantially the same as the inside diameter of the cylincrical outlet of the bag. As shown in the FIGURE the spike is beveled at its edge thereof to provide a point which aids in penetrating the membrane of the bag.

In my improved filter the outer surface 14 of the spike, that is the surface which is to contact the bag opening during insertion of the filter and during the transfusion of the blood, has a roughened surface. The outer surface of my spike is roughened from about 50 to 200 microinches and preferable from between 90 and 130 microinches. If the filter is molded the mold for the spike is roughened to the desired degree to impart the desired roughness to the surface of the spike. If the spike is molded in a smooth condition it may be roughened by sand blasting or other means well known in the art.

The roughness of the surface of the spike of my improved blood filter is measured using a surface profileometer. This is a standard instrument used to measure the roughness of various surfaces.

The blood filters themselves are also made from plastic materials which are inert to blood such as the polyolefin materials or the polycarbonate materials and the like. The outer surface of the spike must be roughened from about 50 microinches to about 200 microinches. If less than a 50 microinch roughness is used it is extremely difficult to insert the spike fully into the blood bag whereas a rougher than 200 microinch surface, though the spike will readily penetrate the bag, it is not positively held even under the slightest pressure in the bag.

To show the ease of insertion and holding power of my improved blood inlet spike a series of tests were conducted using both sterilized and non-sterilized filters. The spikes of all filters tested had their outer surface roughened to 110 ± 20 microinches. Each filter spike was inserted into five ports of various blood bags. The blood bags used had outlet ports varying in diameter from 0.188 inch to 0.208 inch. In each instance the spike was inserted into a port of a bag and approximately 500 mm. Hg pressure placed on the bag. Nine filters were tested so that a total of 45 insertions were accomplished. Two of the 45 insertions required slight force, the remaining 43 were readily inserted in the blood bag ports. None of the filters tested failed or were forced out of the port by the application of the pressure to the blood bag.

Having thus described the invention, what is claimed is:

1. In a blood filter of the type having an inlet spike for insertion into an outlet of a blood bag, said spike being made from a plastic material selected from the group consisting of polyoelifins and polycarbonates, the improvement comprising the outer surface of said spike, that is the surface which is to contact the bag opening during insertion of the filter, having a uniformly roughened finish of from 50 to 200 micro-inches, whereby the spike may be inserted into the outlet without the use of a lubricant.

2. A blood filter according to claim 1 wherein the finish of the inlet spike is from 90 to 130 microinches.

* * * * *